(12) United States Patent
McManus

(10) Patent No.: US 6,383,997 B1
(45) Date of Patent: May 7, 2002

(54) HIGH LATHERING ANTIBACTERIAL FORMULATION

(75) Inventor: Marjorie McManus, Bloomfield, NJ (US)

(73) Assignee: Dragoco Gerberding & Co. AG (DE)

( * ) Notice: Subject to any disclaimer, the term of this patent is extended or adjusted under 35 U.S.C. 154(b) by 0 days.

(21) Appl. No.: 09/897,533

(22) Filed: Jul. 2, 2001

(51) Int. Cl.$^7$ .............................. C11D 3/43; C11D 3/48; C11D 1/94

(52) U.S. Cl. ................ 510/131; 510/130; 510/135; 510/138; 510/147; 510/155; 510/159; 510/382; 510/387; 510/388; 510/405; 510/426; 510/432; 510/433

(58) Field of Search ................. 510/130, 131, 510/135, 138, 147, 155, 159, 382, 387, 388, 405, 432, 426, 433

(56) References Cited

U.S. PATENT DOCUMENTS 5,681,802 A * 10/1997 Fujiwara et al. ............ 510/130

* cited by examiner

*Primary Examiner*—Charles Boyer
(74) *Attorney, Agent, or Firm*—Pendorf & Cutliff

(57) ABSTRACT

An alcohol based antibacterial liquid formulation with high lathering properties, containing an antibacterial agent, an anionic surfactant, moisturizers, skin conditioners, and a high level of alcohol for frequent use in disinfecting the hands and body. More specifically, the present invention relates to a mild, lathering formulation having high content of a low carbon alcohol, an antibacterial agent and at the same time, having an anionic surfactant to make it lather. The formulation is designed to be used with water to enhance the lathering of the solution, while disinfecting at the same time.

11 Claims, No Drawings

HIGH LATHERING ANTIBACTERIAL FORMULATION

FIELD OF THE INVENTION

The present invention relates to an alcohol based antibacterial liquid formulation, which exhibits high lathering properties. More specifically, the invention concerns an alcohol based liquid formulation, which can be formulated with a reduced overall surfactant level yet, achieves high lathering properties and exhibits good antibacterial properties. The formulation is suitable for frequent use in disinfecting the hands and body.

DESCRIPTION OF THE RELATED ART

Liquid formulations for disinfecting the hands and body have been in existence in one form or another throughout the history of humankind. The use of alcohol as an anti-microbial dates to biblical times. Studies have shown that use of ethyl or propanol is very effective in reducing acquired microbial flora on the hands. Use of alcohol as a hand dip was in vogue in the United States in the early years of this century. A common complaint after the use of an alcohol dip was drying and chapping of the hands. Alcohol hand dips rapidly declined in popularity when new liquid soaps containing anti-microbials were introduced.

More recently, alcohol and chlorhexidine gluconate compositions have been developed due to their long lasting efficacy and rapid anti-microbial effect. However, the failure of many bacteria to respond to these compositions and the call for the restricted use of antibiotics has resulted in a decline in the use of topical products containing chlorhexidine gluconate.

In the case of disinfecting hands and skin, an antibacterial agent is desired which kills the widest possible range of microorganisms, in the least possible time, without toxicity, irritation, or other hazards.

Hand wash formulations have been developed using triclosan as an antibacterial agent. Triclosan has a broad-spectrum activity against a variety of microorganisms. However, triclosan has very poor solubility in water and generally requires formulation additives to solubilize it. To solubilize triclosan, it is conventional to use a surfactant, usually in an amount of 15–30% of the formulation.

While some surfactants provide good lathering performance and are effective in emulsifying and removing oily dirt from the skin, they also tend to remove lipids and natural oils from the skin and thus dehydrate the skin. Many surfactants also have a hygroscopic effect, removing water from the skin, further drying the skin. As a result, the skin becomes tight, or taut, due to the emulsification and hygroscopic effects of the surfactants.

While it is important that these compositions contain a good cleansing surfactant system (generally containing at least one anionic surfactant and preferably at least an additional amphoteric surfactant), such compositions should ideally also contain a component beneficial to the skin, e.g., component that will counteract the "dry" feeling associated with a good cleansing surfactant.

The addition of skin conditioning components can further improve the skin mildness of these surfactants, but would further degrade lathering and lathering of any alcohol-based formulation, which would already have poor lathering, and lathering properties.

That is, alcohol based formulations are difficult to formulate into lather-producing or foam-producing products because the alcohol has a natural tendency to kill the foam. The addition of alcohol to a surfactant containing formulation will interfere with the lather forming ability of the surfactant. This foam suppression is undesirable because consumers often associate foam and lather with cleansing ability, and tend to prefer foam or lather producing products.

The introduction of an antibacterial into the equation results in additional problems for mildness, lather, and efficacy. Also, certain surfactants have deactivating effects on the degerming properties of the antibacterial agent.

Thus, a need exists for liquid formulations which will produce a rich foam or lather, which are effective antibacterial cleansers, and which are very mild to the skin even when used repeatedly. In particular, it is desirable to provide such a product, which contains both emollients and humectants, which are effective for re-moisturizing and inhibiting dehydration of the skin.

By way of example, the U.S. Pat. No. 5,403,864 to Bruch et al., entitled "Rapidly-Acting Topical Antibacterial Formulation," teach that ethyl and n-propyl are the most effective alcohols for reducing the bacterial flora on the hands.

The objects of the Bruch et al. invention are to provide an antibacterial formulation that is effective against a broad range of microorganisms, including those pathogenic microorganisms that resist conventional antibacterial formulations; that is easily applied as a topical formulation; and that acts within seconds rather than minutes.

The Bruch et al. formulation comprises triclosan, chloroxylenol, and an alcohol or alcohol mixture. The formulation further contains emollients and humectant ingredients to reduce the normal drying and defatting characteristics of the alcohol. The formulation also contains surfactants as emulsifiers, perfuming agents, and chelating agents.

This reference is limited to teaching liquids of poorly lathering formulations, which do not lather in the manner of a hand soap.

U.S. Pat. No. 5,955,408 to Kaiser et al. entitled "Triclosan Skin Formulation with Enhanced Efficacy" discloses the poor solubility of triclosan in aqueous solvent other than water, and that surfactants which are usually added to solubilize triclosan are skin irritants. Kaiser et al. minimizes this problem (and dissolves triclosan in formulations having about 70% of aqueous solvent other than water) by using aqueous solvents other than water and lower levels of surfactants, preferably less than 10%, to solubilize triclosan. Kaiser et al. use lower than optimal amounts of alcohol, and thus, the disclosed formulations are in need of improvement.

U.S. Pat. No. 5,747,435 to Patel, entitled "Mild Lathering and Conditioning Detergents," teaches a clear or opacified product, which may contain triclosan as anti-dandruff therapeutic agent. As can be seen from the title, the ability to lather is limited.

U.S. Pat. No. 5,994,286 to Desai et al. entitled, "Antibacterial Formulation containing triclosan and Tocopherol," teaches an antibacterial cleaning formulation comprising a surfactant, triclosan, and tocopherol and a process for inhibiting the color degradation of triclosan. The Desai et al. formulation does not include alcohol.

Lastly, U.S. Pat. No. 5,968,539 to Beerse et al. entitled, "Mild, Rinse-Off Antibacterial Liquid Cleaning Formulations which provide residual benefit versus gram negative bacteria," teaches formulations wherein the preferred antimicrobial is triclosan. Beerse et al. fail to produce an antibacterial formulation that is mild to the skin.

While these formulations fulfill their respective, particular objectives and requirements, the aforementioned patents do not describe an alcohol based liquid formulation that exhibits improved mildness to the skin with high lathering properties, and good antibacterial effect.

Therefore, it can be appreciated that there exists a continuing need for a liquid formulation, which exhibits high lathering, good cleaning, and good antibacterial properties, and preferably also good clarity, and which can be used frequently because it exhibits improved mildness.

SUMMARY OF THE INVENTION

In view of the foregoing disadvantages inherent in the known types of liquid formulations in the prior art, the present inventors discovered a unique alcohol-based antibacterial liquid formulation, having improved mildness, with good cleaning, high lathering, and good antibacterial properties. In addition, the present inventors created a method for preparing such a formulation, and a method of cleaning the skin with such formulation.

Unexpectedly, Applicants have found that a combination of a high level of a low carbon alcohol, specified types of surfactants in specified ratios, and a specified antibacterial agent provide a high lathering formulation that is mild to the skin and has good antibacterial properties.

As was discussed above, triclosan has very poor solubility in aqueous solvent other than water and generally requires the presence of surfactant to solubilize it.

The surfactant system in the formulation of the present invention comprises a synergistic mixture of two or more surfactants. A first surfactant is selected for high solubilization of hydrophobic antibacterial agent, e.g., triclosan. A second solvent acts to aid in the solubilization of the first surfactant in aqueous solvent other than water, such that the total amount of surfactants is minimized. This two-stage solubilizing effect is important as it aids in the long-term shelf stability of the formulation, as well as in imparting optical clarity of the formulation.

The formulation of the present invention preferably contains a balanced molar proportion of a first anionic surfactant and a second amphoteric surfactant, which preferably make the formulation crystal clear (although the formulation can be opaque if desired).

The concentration of surfactant in the overall composition is dependent on a number of factors including the concentration of aqueous solvent other than water and the level of antibacterial agent.

The aqueous solvent other than water, preferably a low carbon alcohol, assists in improving the dispersability and/or miscibility of the aqueous solvent other than water insoluble antibacterial agent using a mechanism that is different from the mechanism used by the surfactant.

The present invention concerns an antibacterial liquid formulation:
comprising a high amount of a low carbon alcohol;
an antibacterial agent;
an anionic surfactant;
an amphoteric surfactant; and
a preservative, preferably one or more of methylparaben, propylparaben, ethylpareben, butylparaben, sodium benzoate, potassium sorbate, disodium salt of ethylenediaminetetraacetic acid, chloroxylenol, sodium benzoate, DMDM Hydantoin, 3-iodo-2-propylbutyl carbamate, potassium sorbate, chlorhexidine digluconate, the alkyl esters of para-hydroxybenzoic acid (the parabens, e.g. butylparaben, methylparaben and propylparaben) are preferred and may be used alone or in combination, propyl-p-hydroxybenzoates or sorbic acid, and preferably a combination of methylparaben and propylparaben.

The resulting liquid formulation of the present invention is clear and has high lathering properties despite the high content of alcohol.

Preferably, the present invention concerns an antibacterial liquid formulation comprising:
from about 40 parts to about 80 parts by weight of a low carbon alcohol;
from about 0.05 parts to about 0.3 parts of methylparaben;
from about 0.05 parts to 0.3 parts of propylparaben;
from about 2.0 parts to about 4.0 parts by weight of an antibacterial agent;
from about 0.05 parts to about 1.5 parts by weight of a thickener;
from about 15 parts to about 40 parts by weight of an anionic surfactant; and
from about 6 parts to about 12 parts by weight of an amphoteric surfactant.

As such, the general purpose of the present invention, which will be described subsequently in greater detail, is to provide a new and improved alcohol based antibacterial liquid formulation that lathers in the same manner as soap, and a method of preparing the formulation, and a method of cleaning the skin with such formulation, which has all the advantages of the prior art and none of the disadvantages.

The present invention provides an antibacterial liquid formulation comprising a high concentration of a low carbon alcohol, an antibacterial agent, a thickener, at least one anionic surfactant, and an amphoteric surfactant.

Further, the present invention provides a method for disinfecting the skin comprising the steps of applying to the skin a cleaning effective amount of the above-described formulation for disinfecting the hands and body.

The foregoing has outlined rather broadly the more pertinent and important features of the present invention in order that the detailed description of the invention that follows may be better understood, and so that the present contribution to the art can be more fully appreciated. Additional features of the invention that will be described hereinafter form the subject matter of the claims of the invention. It should be appreciated by those skilled in the art that the conception and the specific embodiments disclosed might be readily utilized as a basis for modifying or formulating other liquid formulations for carrying the same purposes of the present invention. It should also be realized by those skilled in the art that such equivalent formulations do not depart from the spirit and scope of the invention as set forth in the appended claims.

DETAILED DESCRIPTION OF THE INVENTION

The present invention concerns a high lathering antibacterial liquid formulation comprising, based on 100 parts total composition:
from about 40 parts to about 80 parts by weight of a low carbon alcohol;
a preservative;
an antibacterial agent;
a thickener;
an anionic surfactant; and an amphoteric surfactant In a preferred embodiment of the present invention, the high lathering antibacterial liquid formulation of the present invention comprises:

from about 40 parts to about 80 parts by weight of a low carbon alcohol;

methylparaben;

propylparaben;

an antibacterial agent;

a thickener;

an anionic surfactant; and an amphoteric surfactant.

In a more preferred embodiment of the present invention, the high lathering antibacterial liquid formulation comprises with all parts being parts by weight based on 100 parts total composition:

from about 40 parts to about 80 parts by weight of a aqueous solvent other than water, preferably a low carbon alcohol;

from about 0.05 parts to about 0.3 parts by weight of methylparaben;

from about 0.05 to about 0.15 parts by weight of propylparaben;

from about 2.0 parts to about 4.0 parts by weight of an antibacterial agent;

from about 0.05 parts to about 1.5 parts by weight of a thickener;

from about 15 parts to about 40 parts by weight of an anionic surfactant; and from about 6 parts to about 12 parts by weight of an amphoteric surfactant; and optionally, humectants, fragrance, colorants, or fragrances;

wherein the molar ratio parabens/surfactants are preferably 10:90 to 90:10, more preferably 70:30 to 30:70.

The Aqueous Solvent Other Than Water

Examples of suitable aqueous solvents other than water include glycols (such as propylene glycol, ethoxydiglycol, butylene glycol, triethylene glycol) and lower alcohols; triglycerides; acetones; and combinations of these. The preferred aqueous solvent other than water is a lower alcohol selected from the group consisting of ethanol, methanol, propanol, isopropanol and ethyl alcohol with diethylphthalate as an optional denaturant, such as those sold under the trade name SD 39C.

The low carbon alcohol is present in the formulation preferably in an amount of 40–80 above by percent weight based on 100 parts total composition.

Antibacterial Agent

The antibacterial agent is present in the formulation in quantities effective to inhibit the growth and/or kill bacteria on the skin. Although various known antibacterial agents can be employed, such as chloroxylenol and the halogenated carbanilides, the antibacterial agents employed in the present invention are generally halo-substituted dihydric phenol compounds and most preferably, a dihydric phenol 2,4,4'-trichloro-2'-hydroxydiphenyl ether (triclosan).

The antibacterial agent is present in the formulation in an amount of from about 2.5 parts to about 3.5 parts by weight based on 100 parts total composition.

Anionic Surfactant

The anionic surfactant which is employed in the aqueous liquid composition is any high lathering anionic surfactant such as a long chain sulfate, sulfonate, isethionate, carboxylate, taurate, sulfosuccinate, phosphate and the like. Alkoxylated, preferably ethoxylated materials, are even more preferred. The most preferred material is an alkyl sulfate having an average of -about 8 to 16 carbon atoms, preferably an average of 10 or 12 carbon atoms, most preferably normal alkyl. It is preferred that this material be ethoxylated with 1 to 4, preferably 2 or 3, average number of ethoxy groups. The cation is preferably an alkali metal or amine such as sodium, potassium or triethanolamine, most preferably triethanolamine.

Preferred additional anionic surfactants for use in the present invention include alkyl glyceryl ether sulfonate, ammonium lauryl sulfate, ammonium laureth sulfate, triethylamine lauryl sulfate, triethylamine laureth sulfate, triethanolamine lauryl sulfate (Standapol T), triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, and combinations thereof.

The preferred amount of surfactant varies to some degree with the class of surfactant employed, the concentration of non-aqueous solvent and the concentration of the antimicrobial agent.

The amount of anionic surfactant in the present invention is from about 20 parts to about 30 parts by weight, preferably 25 parts by weight based on 100 parts by weight based on 100 parts total composition.

Amphoteric Surfactant

The present invention uses the amphoteric surfactant preferably as a co-active surfactant. The preferred amphoteric surfactant will be a betaine, preferably selected from the group consisting of amidocarboxybetaines, alkyl betaines, amidopropyl betaines, amidopropyl sultaines, and sulfobetaines. In the present invention, the preferably amphoteric surfactant is amidocarboxybetaines, particularly cocoamidodimethylcarboxymethylbetaines (COCOMIDOPROPYLBETAINE), such as those sold by Goldschmidt Co. under the trade name Tegobetaine.

The amount of amphoteric surfactant in the present invention is from about 6 parts to about 12 parts by weight based on 100 parts total composition.

Preservative

Suitable preservatives for use in the formulation of the present invention include, but are not limited to, preferably one or more of methylparaben, propylparaben, ethylpareben, butylparaben, sodium benzoate, potassium sorbate, disodium salt of ethylenediaminetetraacetic acid, chloroxylenol, sodium benzoate, DMDM Hydantoin, 3-iodo-2-propylbutyl carbamate, potassium sorbate, chlorhexidine digluconate, the alkyl esters of para-hydroxybenzoic acid (the parabens, e.g. butylparaben, methylparaben and propylparaben) are preferred and may be used alone or in combination, propyl-p-hydroxybenzoates or sorbic acid, and preferably a combination of methylparaben and propylparaben.

The invention contains from about 0.05 parts to about 0.3 parts of methylparaben and from about 0.05 parts to about 0.2 parts of propylparben based on 100 parts total composition.

Thickener

The selection of the proper thickening agent provides the antibacterial formulation with the desired viscosity values. The polymer/viscosity—inducing agent or thickener—can be selected from the group consisting of hydropropylcellulose, carboxymethylcellulose, sodium carboximethylcellulose, carbomer, tragacanth, and the like.

In the present invention, a pharmaceutical grade hydroxypropylcellulose is preferably used as a thickener. This hydroxypropylcellulose was found to be the most stable thickener because it does not precipitate in presence of high alcohol levels and surfactants. Regular carbopols precipitated when surfactants and high levels of alcohol were mixed together.

There are some new generations of Carbopols that are salt tolerant, such as CARBOPOL 2020 ETD, that are capable of thickening surfactants systems without precipitating, they give very poor forming.

In addition to being a thickener, hydroxypropylcellulose is a good and logical thickener choice because it fixes triclosan to the skin.

The preferable hydroxypropylcellulose is sold by Aqualon under the trade name Klucel. The amount of thickener in the present invention is from about 0.05 parts to about 1.5 parts by weight, preferably 1.0 part per weight based on 100 parts of the total formulation.

Other agents may also be present in the formulation. For example, additional non-preferred anionic surfactants, emollients, humectant, and the like.

Humectants

Another component of the compositions of the present invention is a humectant. As used herein, "humectant" means ingredients suitable for application to the hair or skin, which promotes retention of water by the hair, or skin. The humectants for use herein will be water-soluble. Even though these materials are defined herein as humectants, they can also possess emolliency or moisturizing, or other conditioning, or other properties.

Humectants are well known in the art of skin care and conditioning. Examples of humectants useful herein include materials such as urea; guanidine; glycolic acid and glycolate salts (e.g. ammonium and quaternary alkyl ammonium); lactic acid and lactate salts (e.g. sodium, ammonium, and quaternary alkyl ammonium); aloe vera in any of its variety of forms (e.g., aloe vera gel); polyhydroxy alcohols such as sorbitol, glycerol, hexanetriol, propylene glycol, butylene glycol, hexylene glycol, and the like; polyethylene glycol; pyrrolidone carboxylic acids and their salts (e.g., sodium pyrrolidone carboxylic acid); sugars and starches; sugars and starches and their derivatives (e.g., honey extract, alkoxylated glucose); 6-(N-acetylamino)-4-oxahexyltrimonium chloride; hyaluronic acid; chitin, starch-grafted sodium polyacrylates such as Sanwet (RTM) IM-1000, IM-1500, and IM-2500 (available from Celanese Superabsorbent Materials, Portsmouth, Va.); lactamide monoethanolamine; acetamide monoethanolamine; propoxylated glycerol ; and mixtures thereof.

Preferred humectants useful in the compositions of the present invention are the C3–C6 diols and triols. More preferred as humectants are the C3–C6 diols and triols selected from the group consisting of propylene glycol, 1,3-dihydroxypropane, glycerin, urea; honey extract, butylene glycol, hexylene glycol, 1,4-dihydroxyhexane, 1,2,6-hexanetriol, and mixtures thereof. Most preferred as humectants are those selected from the group consisting of glycerin, urea, honey extract, butylene glycol, hexylene glycol, and mixtures thereof.

Emollients

Exact levels of emollient, if present, will depend upon the material chosen with consideration being given to the effects upon lathering and lathering of the composition. Emollients in skin and personal care are materials, which are used to replace or add to lipids and natural oils in the skin or hair. The term emollient, as used herein, is intended to include conventional lipid materials (e.g., fats, waxes, and other water insoluble materials), polar lipids (e.g., lipid materials which have been hydrophylically modified to render them more water soluble), silicones and hydrocarbons. Without being limited by theory, it is believed that these emollient materials help to provide a skin conditioning benefit by depositing upon the skin or hair during the cleansing and rinsing processes.

A wide variety of emollient materials are suitable for use in the compositions of the present invention. Examples of conventional emollients include C8–30 alkyl esters of C8–30 carboxylic acids; C1–6 diol monoesters and diesters of C8–30 carboxylic acids; monoglycerides, diglycerides, and triglycerides of C8–30 carboxylic acids, cholesterol esters of C8–30 carboxylic acids, cholesterol, and hydrocarbons. Examples of these materials include diisopropyl adipate, isopropyl myristate, isopropyl palmitate, ethylhexyl palmitate, isodecyl neopentanoate, C12–15 alcohols benzoate, diethylhexyl maleate, PPG-14 butyl ether, PPG-2 myristyl ether propionate, cetyl ricinoleate, cholesterol stearate, Softigen 767, SME 253, cholesterol isostearate, cholesterol acetate, jojoba oil, cocoa butter, shea butter, lanolin, and lanolin esters.

An especially useful group of emollients are the so-called "polar lipids" which contain hydrophilic moieties such as hydroxy groups, carbonyl groups, and ether linkages. Preferred classes of these polar lipids include C10–20 alcohol monosorbitan esters, C10–20 alcohol sorbitan diesters, C10–20 alcohol sorbitan triesters, C10–20 alcohol sucrose monoesters, C10–20 alcohol sucrose diesters, C10–20 alcohol sucrose triesters, and C10–20 fatty alcohol esters of C2–C6 2-hydroxy acids. Non-limiting examples of these polar lipids are sorbitan diisostearate, sorbitan dioleate, sorbitan distearate, sorbitan isostearate, sorbitan laurate, sorbitan oleate, sorbitan palmitate, sorbitan sesquioleate, sorbitan sesquistearte, sorbitan stearate, sorbitan triiostearte, sorbitan trioleate, sorbitan tristeate, sucrose cocoate, sucrodilaurate, sucrose distearate, sucrose laurate, sucrose myristate, sucrose oleate, sucrose palmitate, sucrose ricinoleate, sucrose stearate, sucrose tribehenate, sucrose tristearate, myristyl lactate, stearyl lactate, isostearyl lactate, cetyl lactate, palmityl lactate, cocoyl lactate, and mixtures thereof. Other polar lipids are the C10–20 alkyl pidolates (i.e. pyrrolidone carboxylate esters, examples of which are myristyl pidolate, cetyl pidolate, lauryl pidolate, and stearyl pidolate). Yet other polar lipids are alkyl C1–3 esters of panthenol such as panthenyl triacetate (which is the triacetyl ester of panthenol). Especially preferred among the polar lipids are isostearyl lactate (available as Pationic Ill., from RITA Corp), sorbitan laurate (available as Arlacel 20 from ICI Americas), lauryl pyrrolidone carboxylic acid (available as lauryl pidolate from UCIB Corp.), panthenyl triacetate (available as D-panthenyl triacetate from Induchem), and mixtures thereof.

Also useful are silicones including non-volatile silicones such as dimethicone copolyol; dimethylpolysiloxane; diethylpolysiloxane; high molecular weight dimethicone (average molecular weight from about 200,000 to about 1,000,000 and, preferably, from about 300,000 to about 600,000) which can have various end-terminating groups such as hydroxyl, lower $C_1$–$C_3$ alkyl, lower $C_1$–$C_3$ alkoxy and the like; mixed $C_1$–$C_3$ alkyl polysiloxane (e.g., methylethylpolysiloxane); phenyl dimethicone and other aryl dimethicones; dimethiconol; fluorosilicones; and mixtures thereof.

Preferred are non-volatile silicones selected from the group consisting of dimethicone copolyol, dimethylpolysiloxane, diethylpolysiloxane, high molecular weight dimethicone, mixed $C_1$–$C_{30}$ alkyl polysiloxane, phenyl dimethicone, dimethiconol, and mixtures thereof. More preferred are non-volatile silicones selected from dimethicone, dimethiconol, mixed $C_1$–$C_{30}$ alkyl polysiloxane, and mixtures thereof. Especially preferred is dimethiconol, which is a dimethyl silicone polymer, terminated with hydroxyl groups. Dimethiconol is available as Q2-1401 Fluid, a solution of 13 percent ultra-high-viscosity dimethiconol in volatile cyclomethicone fluid as a carrier; as Q2-1403 Fluid, a solution of ultra-high-viscosity dimethiconol fluid in dimethicone (both sold by Dow Corning Corporation); and as other custom blends (e.g. 10% dimethiconol in dimethicone). Non-limiting examples of silicones useful herein are described in U.S. Pat. No. 5,011,681, to Ciotti et al., issued Apr. 30, 1991, which has already been incorporated by reference.

Among the emollients preferred are those selected from the group consisting of dimethicone, dimethiconol, diisopropyl adipate, isopropyl myristate, myristyl myristate, cetyl ricinoleate, sorbitan distearte, sorbitan dilaurate, sorbitan stearate, sorbitan laurate, suscrose laurate, sucrose dilaurate, sodium isostearyl lactylate, lauryl pidolate, sorbitan stearate, panthenyl triacetate, and mixtures thereof. More preferred are those selected from the group consisting of sorbitan laurate, sucrose laurate, sodium isostearyl lactylate, lauryl pidolate, sorbitan stearate, panthenyl triacetate, and mixtures thereof. Most preferred are those selected from the group consisting of sodium isostearyl lactylate, lauryl pidolate, sorbitan stearate, panthenyl triacetate, and mixtures thereof.

Other skin conditioning agents which may optionally be present in the composition of the invention include allantoin, d- or dl-panthenol, sodium-2-pyrrolidone carboxylic acid, Quaternium 70 (Ceraphyl 70, trademark of Van Dyk Chemical), cocoamidopropyl betaine (Velvetex BA-35, trademark of Henkel, Inc.) and the like.

The present formulation is applied to the skin surface to be treated in a conventional manner, as one would apply any hand wash or soap. Preferably, the formulation is dispensed from a bottle or other dispenser and worked into the hands for sufficient time to remove soil and kill microorganisms present on the skin. Water is used to assist in the formation of lather.

The present invention also contains a method of preparing an antibacterial liquid formulation for disinfecting the hands and body, comprising the steps of:

A) adding into a vessel:

a high amount of a low carbon alcohol;

an antibacterial agent;

an anionic surfactant;

an amphoteric surfactant; and a preservative, preferably one or more of methylparaben, propylparaben, ethylpareben, butylparaben, sodium benzoate, potassium sorbate, disodium salt of ethylenediaminetetraacetic acid, chloroxylenol, sodium benzoate, DMDM Hydantoin, 3-iodo-2-propylbutyl carbamate, potassium sorbate, chlorhexidine digluconate, the alkyl esters of para-hydroxybenzoic acid (the parabens, e.g. butylparaben, methylparaben and propylparaben) are preferred and may be used alone or in combination, propyl-p-hydroxybenzoates or sorbic acid, and preferably a combination of methylparaben and propylparaben.

B) mixing the ingredients; adding slowly from about 0.05 parts to about 1.5 parts by weight of thickener; mixing the ingredients until the solution is homogenous; adding from about 15 parts to about 40 parts by weight of an anionic surfactant; adding from about 6 parts to about 12 parts by weight of an amphoteric betaine; and stirring until the solution is uniform.

Method of Use

In its method aspect, the present invention comprises a method of washing the skin by contacting the skin with an amount of the liquid antibacterial formulation herein, which is an effective disinfectant for the skin. The method of disinfecting the skin comprises the steps of:

applying to the skin an effective amount of the cleaning formulation of the present invention;

maintaining contact between the formulation and the skin for sufficient time to kill all microorganisms present on the skin.

adding water and rubbing the surface, thereby removing the dirt from the surface, followed by rinsing the formulation from the skin.

EXAMPLE 1

The following ingredients were assembled in the following amounts:

| Item | Ingredient | % | Supplier |
|---|---|---|---|
| 1 | Sd 39 C alcohol | 62 | |
| 2 | Methylparaben | 0.2 | |
| 3 | Propylparaben | 0.1 | |
| 4 | triclosan | 3.0 | Ciba Geigy |
| 5 | Klucel | 1.0 | Aqualon |
| 6 | Standapol T | 25 | Henkel |
| 7 | Tego Betaine L-7 | 8.7 | Goldschmidt |
| Total | | 100 | |

Formula preparation: In Example 1, 100 ml of a high lathering cleaning formulation was produced. Thus, the above percentages are simply converted into ml, with each percent converting to one ml. Ingredients 1–4 were mixed in a mixing vessel. Ingredient 5 was added slowly under agitation until the solution was homogeneous. Ingredients 6 and 7 were added under agitation until the solution was uniform. An antibacterial formulation with good lathering properties was obtained.

EXAMPLE 2

The following ingredients were assembled in the following amounts:

| Item | Ingredient | % | Supplier |
|---|---|---|---|
| 1 | Sd 39 C alcohol | 65 | |
| 2 | Methylparaben | 0.2 | |
| 3 | Propylparaben | 0.1 | |
| 4 | Klucel | 1.0 | Aqualon |

-continued

| Item | Ingredient | % | Supplier |
|---|---|---|---|
| 5 | Standapol T | 25 | Henkel |
| 6 | Tego Betaine L-7 | 8.7 | Goldschmidt |
| Total | | 100 | |

Formula preparation: In Example 2, 100 ml of a high lathering cleaning formulation were produced. Thus, the above percentages are simply converted into ml, with each percent converting to one ml. Ingredients 1–3 were mixed in a mixing vessel. Ingredient 4 was added slowly under agitation until the solution was homogeneous. Ingredients 5 and 6 were added under agitation until the solution was uniform. A lathering antibacterial formulation was obtained.

EXAMPLE 3

The following ingredients were assembled in the following amounts:

| Item | Ingredient | % | Supplier |
|---|---|---|---|
| 1 | Sd 39 C alaohol | 65 | |
| 2 | Methhylparaben | 0.2 | |
| 3 | Propylparaben | 0.1 | |
| 4 | Klucel | 1.0 | Aqualon |
| 5 | Standapol T | 25 | Henkel |
| 6 | Velvetex BA 35 | 7.7 | Henkel |
| 7 | Fragrance | 1.0 | Dragoco |
| Total | | 100 | |

Formula preparation: In Example 3, 100 ml of a high lathering cleaning formulation were produced. Thus, the above percentages are simply converted into ml, with each percent converting to one ml. Ingredients 1–3 were mixed in a mixing vessel. Ingredient 4 was added slowly under agitation until the solution was homogeneous, and Klucel is fully hydrated. Ingredients 5 and 6 were added under agitation until the solution was uniform. A clear lathering antibacterial formulation was obtained.

EXAMPLE 4

The following ingredients were assembled in the following amounts:

| Item | Ingredient | % | Supplier |
|---|---|---|---|
| 1 | Sd 39 C alcohol | 60 | |
| 2 | Methylparaben | 0.2 | |
| 3 | Propylparaben | 0.1 | |
| 4 | Triclosan | 3.05 | |
| 5 | Klucel | 2.0 | Aqualon |
| 6 | Standapol T | 20 | Henkel |
| 7 | Tego Betaine L-7 | 8.7 | Goldschmidt |
| 8 | Softigen 767 | 3.0 | Condea Vista |
| 9 | SME 253 | 2.0 | GE Silicones |
| 10 | Fragrance | 1.0 | Dragoco |
| Total | | 100 | |

Formula preparation: In Example. 4, 100 ml of a high lathering cleaning formulation were produced. Thus, the above percentages are simply converted into ml, with each percent converting to one ml. Ingredients 1–4 were mixed in a mixing vessel. Ingredient 5 was added slowly under agitation until the solution was homogeneous. Ingredients 6 to 10 were added under agitation until the solution was uniform. An opaque moisturizing lathering antibacterial formulation was obtained. The formulation is slightly thicker than the original formulation, but the lathering properties did not change.

EXAMPLE 5

The following ingredients were assembled in the following amounts:

| Item | Ingredient | % | Supplier |
|---|---|---|---|
| 1 | Sd 39 C alaohol | 65 | |
| 2 | Methylparaben | 0.2 | |
| 3 | Propylparaben | 0.1 | |
| 4 | Klucel | 2.0 | Aqualon |
| 5 | Standapol T | 25 | Henkel |
| 6 | Tego Betaine L-7 | 7.7 | Henkel |
| Total | | 100 | |

Formula preparation: In Example 5, 100 ml of a high lathering cleaning formulation were produced. Thus, the above percentages are simply converted into ml, with each percent converting to one ml. Ingredients 1–3 were mixed in a mixing vessel. Ingredient 4 was added slowly under agitation until the solution was homogeneous. Ingredients 5 and 6 were added under agitation until the solution was uniform. A clear lathering antibacterial formulation was obtained.

The above liquid antibacterial formulations are highly preferred, particularly for use as a hand wash because of the convenience and non-messiness. In addition, they have antibacterial properties and are very mild to the skin.

Now that the invention has been described,

What is claimed:

1. A high lathering antibacterial liquid formulation comprising, based on 100 parts total composition:
    a) from about 40 parts to about 80 parts by weight of a low carbon alcohol;
    b) from about 0.05 parts to about 0.6 parts of a preservative;
    c) from about 2.0 parts to about 4.0 parts by weight of an antibacterial agent;
    d) from about 0.05 parts to about 1.5 parts by weight of a thickener;
    e) from about 15 parts to about 40 parts by weight of an anionic surfactant; and
    f) from about 6 parts to about 12 parts by weight of an amphoteric surfactant.

2. A high lathering antibacterial liquid formulation as in claim 1, wherein said preservative is selected from the group consisting of methylparaben, propylparaben, ethylpareben, butylparaben, and combinations of methylparaben and propylparaben.

3. The high lathering liquid formulation of claim 1, wherein said low carbon alcohol is selected from the group consisting of ethanol, methanol, propanol and isopropanol.

4. The liquid formulation of claim 1, wherein said anionic surfactant is selected from the group consisting of alkyl glyceryl ether sulfonate, ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, monoethanolamine cocoyl sulfate, sodium tridecyl benzene sulfonate and sodium dodecyl benzene sulfonate.

5. The liquid formulation of claim 1 wherein said antibacterial agent is triclosan.

6. A high lathering clear antibacterial liquid formulation comprising, based on 100 parts total composition:
   a) from about 40 parts to about 80 parts by weight of a low carbon alcohol;
   b) from about 0.05 parts to about 0.6 parts by weight of methylparaben;
   c) from about 0.05 parts to about 0.6 parts by weight of propylparaben;
   d) from about 2.0 parts to about 4.0 parts by weight of an antibacterial agent;
   e) from about 0.05 parts to about 1.5 parts by weight of a thickener;
   f) from about 15 parts to about 40 parts by weight of an anionic surfactant; and
   g) from about 6 parts to about 12 parts by weight of an amphoteric surfactant.

7. A method of preparing a high lathering antibacterial liquid formulation for disinfecting the hands and body comprising the steps of:
   a) adding into a vessel, based on 100 parts total composition:
      i) from about 40 parts to about 80 parts by weight of a low carbon alcohol;
      ii) from about 0.05 parts to about 0.6 parts by weight of a preservative;
      iii) from about 2.0 parts to about 4.0 parts by weight of an antibacterial agent;
   b) mixing the ingredients;
   c) adding slowly from about 0.05 parts to about 1.5 parts by weight of a thickener;
   d) mixing the ingredients until the solution is homogenous;
   e) adding from about 15 parts to about 40 parts by weight of an anionic surfactant;
   f) adding from about 6 parts to about 12 parts by weight of an amphoteric surfactant; and
   g) stirring until the solution is uniform.

8. A method as in claim 7 wherein said low carbon alcohol is selected from the group consisting of ethanol, methanol, propanol, and isopropanol.

9. A method as in claim 7 wherein said antibacterial agent is triclosan.

10. A method for disinfecting the skin comprising:
    a) applying to the skin a cleaning effective amount of a high lathering formulation including:
       i) from about 40 parts to about 80 parts by weight of a low carbon alcohol;
       ii) from about 0.05 parts to about 0.6 parts by weight of a preservative;
       iii) from about 2.0 parts to about 4.0 parts by weight of an antibacterial agent;
       iv) from about 0.05 parts to about 1.5 part by weight of a thickener;
       v) from about 15 parts to about 40 parts by weight of an anionic surfactant; and
       vi) from about 6 parts to about 12 parts by weight of an amphoteric surfactant;
    b) rubbing said liquid formulation on the skin to produce lather; and
    c) maintaining contact between the formulation and the skin for sufficient time to kill all microorganisms present on the skin.

11. The method of claim 10, further including adding water and rubbing the skin surface, thereby removing dirt from the skin surface, followed by rinsing the formulation from the skin.

* * * * *